United States Patent [19]

Donini

[11] Patent Number: 4,950,275
[45] Date of Patent: Aug. 21, 1990

[54] BOWEL-ANASTOMOSIS-RING HOLDER PINCERS

[75] Inventor: Ippolito G. Donini, Ducentola di Voghiera, Italy

[73] Assignee: Cyanamid Italia S.p.A., Catania, Italy

[21] Appl. No.: 382,742

[22] Filed: Jul. 19, 1989

[51] Int. Cl.$^5$ ............................................. A61B 17/00
[52] U.S. Cl. ................................. 606/151; 606/208; 606/207
[58] Field of Search ............... 606/108, 151, 153, 197, 606/207, 208

[56] References Cited

U.S. PATENT DOCUMENTS 1,472,380  10/1923  Atwood ............................ 606/207

Primary Examiner—Randall L. Green
Attorney, Agent, or Firm—Beveridge, DeGrandi & Weilacher

[57] ABSTRACT

The invention relates to Bowel-Anastomosis-Ring holder pincers having two pivotally connected arms and a terminal head portion, angled with respect to said arms, wherein said head portion has two jaws which form in combination with one another an elliptical shape, each of said jaws including a lower claw upon which an upper claw is fixed as a staple member, having the same elliptical curvature as the lower claw and slightly inwardly staggered with respect thereto. The upper claws have a circular cross-section and the lower claws have an internal surface with a slightly inwardly concave profile.

4 Claims, 2 Drawing Sheets

BOWEL-ANASTOMOSIS-RING HOLDER PINCERS

This invention broadly relates to surgical pincers and particularly concerns such pincers for manipulating and holding bowel anastomosis rings.

BACKGROUND OF THE INVENTION

Among the technical procedures for bowel suturation, the pressure suturation can be mentioned, namely the pressure butt joining of the anastomosis ends carried out by means of annular devices of various shapes and sizes inserted into the bowel lumen. These devices usually consist of two half-shells and of a central core. The half-shells are introduced into the lumen of the bowel ends and their edges are subsequently clamped onto the central core by means of so-called tobacco-bag strings. Then the two half-shells are brought together and pressure closed, thus enabling the bowel walls to mutually contact and to cure. Thereafter, the ring assembly falls into the bowel lumen and is ejected or it shatters and is progressively eliminated, if the assembly is biodegradable.

The ring suture assemblies frequently mentioned as B.A.R. (Bowel Anastomosis Rings), as presently available, can be used solely in those anatomical areas where an easy surgical access and a particularly large operation room are available. In no way they can be directly positioned by the hands of the surgeon in deep, narrow and/or hardly accessible areas, such as the rectum (pelvis minor) and the esophagus.

Lack of a suitable instrument for use in these areas has been of the utmost importance in the prior art, because sealing of the anastomosis in these areas is a critical aspect for the very life of the patient.

It is an object of this invention to cure this deficiency of the prior art and to make a mechanical instrument and particularly pincers available for insertion of bowel anastomosis rings, adapted to enable such ring assemblies to be easily inserted into hardly accessible organs, such as lower rectum or esophagus, as well as to eliminate any hand contamination.

SUMMARY OF THE INVENTION

This object is attained by means of pincers that, in their basic embodiment, have two pivotally connected arms and a terminal head portion, angled with respect to said arms and comprising and two jaws which form in combination with one another an elliptical shape, each of said jaws including a lower claw upon which an upper claw is fixed as a staple member, having the same elliptical curvature as the lower claw and slightly inwardly staggered with respect thereto.

In the pincers according to the invention, the upper claws have a circular cross-section and the lower claws have a slightly inwardly concave cross-section.

From a geometrical view point, the circles incribed into the two claw pairs and tangent to their internal profiles are concentric.

BRIEF DESCRIPTION OF THE DRAWINGS

Further details and advantages of this invention will be apparent from the following description to be read with reference to the enclosed drawings wherein the preferred embodiments are illustratively but not restrictively shown and wherein.

DESCRIPTION OF THE PREFERRED EMBODIMENTS

Figure 1:
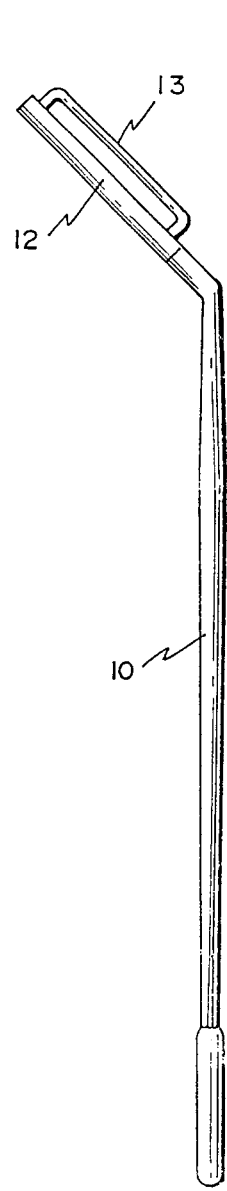
FIG. 1 is a side elevation view of a pincers device according to this invention.

Referring now to the drawings, it can be seen that the pincers of this invention have two pivotally connected arms 10, 11 and a terminal head portion which is the effective operational portion of the pincers.

Figure 2:
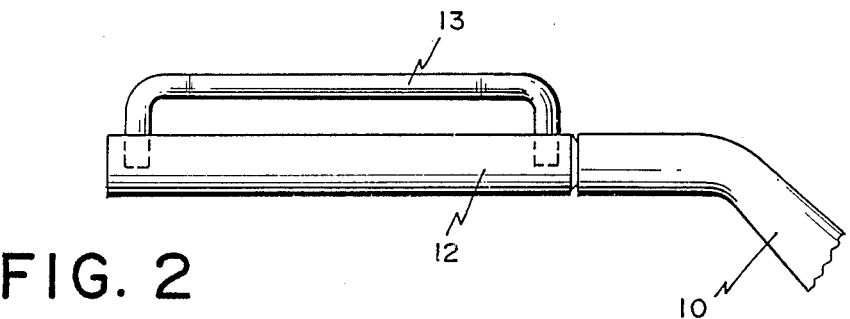
FIG. 2 is an enlarged side elevation view, showing the head portion of the pincers.
Figure 3:
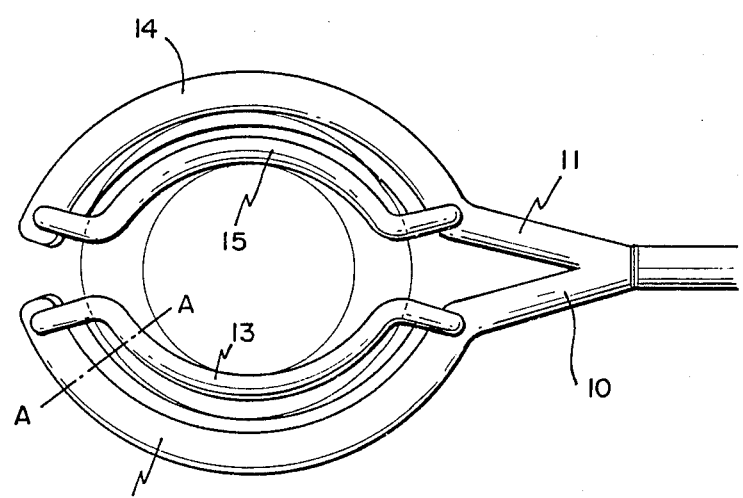
FIG. 3 is an enlarged plan view of the head portion of the pincers.

The operational portion, detailedly shown in FIGS. 2 and 3, consists of two jaws which in combination form an elliptical shape, each including two superposed claws 12, 13 and 14, 15, respectively. The two upper claws 13 and 15 are fixed upon the two lower claws 12 and 14 as staple members and have the same elliptical curvature as the lower claws 12 and 14.

From a geometrical view point, it can be observed from FIG. 3 that, when jaws are in closed condition, the circles inscribed into the two lower claws 12, 14 and into the two upper claws 13, 15 and tangent to their internal profiles are concentric.

Figure 4:
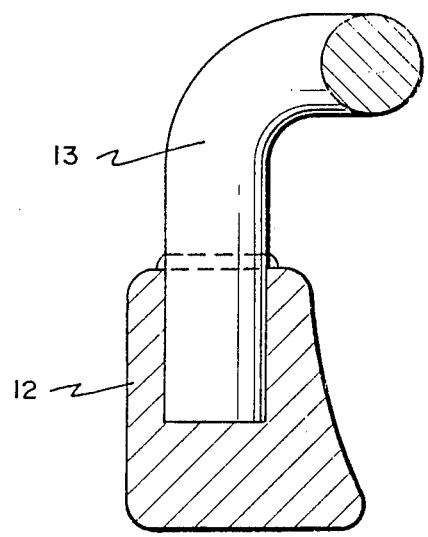
FIG. 4 is a fragmentary view, in partial cross-section along line A—A of FIG. 3, showing the cross-sectional profiles of the jaw claws of the pincers.

The cross-sections of the upper claws 13, 15 are circular, while, as it can be seen in FIG. 4, the inner surfaces of the lower claws 12, 14 have a slightly inwardly concave profile such that, when the jaws are closed, the half-shell of the ring is grasped, pushed upwardly and anchored against the upper, slenderer claw, abutted to the central core of the ring. When this operation is carried out, after the first tobacco-ring string is closed upon the central core, sufficient room is left for the second tobacco-bag string to be closed. In addition, the pincers enable the half-shell to be substained in order to create the indispensable bearing point in absence of which it is not possible to pressure close the ring. This is useful particularly when anastomosis is to be carried out in deep areas (such as in the rectum) or in restricted areas (such as in the thoracic esophagus).

In conclusion, the pincers according to this invention noticeably enlarge the application range of the bowel anastomosis rings and in particular extend it so as to include all those areas where the application of such rings has a strategical relevance. In fact, when the anatomic-surgical conditions permit the rings to be manually positioned, then the employment of alternative as much safe techniques becomes even more possible.

Use of the pincers according to this invention is the rectum and in the esophagus is convenient under various technical aspects:

a. during the ring positioning step, the pincers enable the lower annular half-shell to be easily inserted into the rectum lumen (which is impossible to be manually carried out), in view of a grasping and fixing action upon the upper annular half-shell, already inserted into the colon lumen;

b. upon closure of the second tobacco-bag string, the ring is to be pressure tightened. This action is usually carried out by the surgeon who takes with his fingers the annular shells at four opposed points and exerts a noticeable pressure.

In the above mentioned areas, this action is effectively impossible due to shortage of room and to immobility of the organs, that do not enable the ring to be safely clasped with the fingers. This action becomes possible only when the pincers according to the invention are used as an anvil to bear the distal (with respect to the hands of the surgeon) half-shell. The jaws of the pincers in closed condition act as a "seat" wherein the distal half-shell is positioned. In this manner, it is firmly supported, while the surgeon closes under pressure the proximal half-shell.

Figure 5:
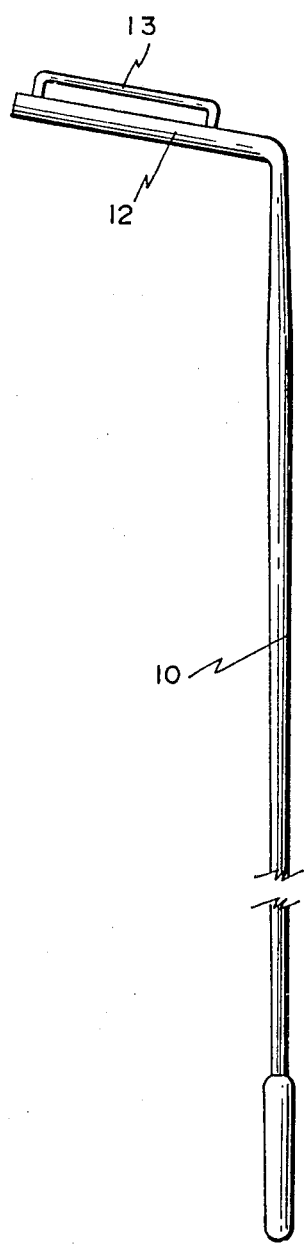
FIG. 5 is a view similar to the view of FIG. 1 showing a different embodiment with a more angled head portion.

From the previous description, it will be easily understood that the angle of the head portion (jaws) with respect to the arms 10, 11 can be different from the one shown in FIG. 1, as it is shown in FIG. 5, and the arms can be longer or shorter to enable hardly accessible and deep areas to be reached. Furthermore, the pincers can be made of such a material as to be disposable.

In the previous description, the preferred emodiments have been disclosed, but it should be understood that changes and modifications can be made by those skilled in the art without departing from the scope of this invention.

I claim:

1. Bowel-Anastomosis-Ring holder pincers having two pivotally connected arms and a terminal head portion, angled with respect to said arms, characterized in that said head portion comprises two jaws which form in combination with one another an elliptical shape, each of said jaws including a lower claw upon which an upper claw is fixed as a staple member, having the same elliptical curvature as the lower claw and slightly inwardly staggered with respect thereto.

2. Bowel-Anastomosis-Ring holder pincers according to claim 1, characterized in that, from a geometrical view point, the lower and upper claws have a curvature such that, in their closed condition, the circles inscribed therein and tangent to their internal profiles are concentric.

3. Bowel-Anastomosis-Ring holder pincers according to claim 1, characterized in that said upper claws have a circular cross-section.

4. Bowel-Anastomosis-Ring holder pincers according to claim 1, characterized in that said lower claws have an internal surface with a slightly inwardly concave profile.

* * * * *